(12) United States Patent
Ichihashi

(10) Patent No.: US 12,097,387 B2
(45) Date of Patent: Sep. 24, 2024

(54) RADIATION TREATMENT PLANNING APPARATUS AND RADIATION TREATMENT APPARATUS

(71) Applicant: Canon Medical Systems Corporation, Otawara (JP)

(72) Inventor: Masahide Ichihashi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 780 days.

(21) Appl. No.: 17/154,158

(22) Filed: Jan. 21, 2021

(65) Prior Publication Data
US 2021/0220672 A1    Jul. 22, 2021

(30) Foreign Application Priority Data
Jan. 22, 2020 (JP) .................. 2020-008528

(51) Int. Cl.
*A61N 5/10* (2006.01)

(52) U.S. Cl.
CPC ......... *A61N 5/1037* (2013.01); *A61N 5/1045* (2013.01)

(58) Field of Classification Search
CPC ... A61N 5/1037; A61N 5/1045; A61N 5/1068
See application file for complete search history.

(56) References Cited

U.S. PATENT DOCUMENTS

2009/0252291 A1* 10/2009 Lu .................. A61N 5/1049
378/65
2012/0106704 A1* 5/2012 Maurer, Jr. ............ G16H 20/30
378/65
2015/0243025 A1* 8/2015 Berlinger ............. G06T 7/0012
382/128
2016/0174921 A1 6/2016 Wikler
2019/0255362 A1* 8/2019 Voronenko ........... A61N 5/1071

FOREIGN PATENT DOCUMENTS

| JP | 10-201863 A | 8/1998 |
| JP | 11-319123 A | 11/1999 |
| JP | 2001-327514 A | 11/2001 |
| JP | 2016-120282 A | 7/2016 |
| JP | 2017-121324 A | 7/2017 |
| JP | 2019-18010 A | 2/2019 |

OTHER PUBLICATIONS

Japanese Office Action issued Oct. 24, 2023 in Japanese Patent Application No. 2020-008528, 5 pages.

* cited by examiner

Primary Examiner — Thaddeus B Cox
Assistant Examiner — Joshua Daryl D Lannu
(74) Attorney, Agent, or Firm — Oblon, McClelland, Maier & Neustadt, L.L.P.

(57) ABSTRACT

A radiation treatment planning apparatus according to one aspect includes a processing circuitry. The processing circuitry obtains time-series medical images. The processing circuitry specifies a first time phase in which radiation irradiation is performed and a second time phase in which no radiation irradiation is performed, in a period corresponding to the time-series medical images based on a positional relationship between a treatment target region and at-risk region of a patient included in the time-series medical images. The processing circuitry generates a treatment plan based on a medical image of the specified first time phase.

14 Claims, 13 Drawing Sheets

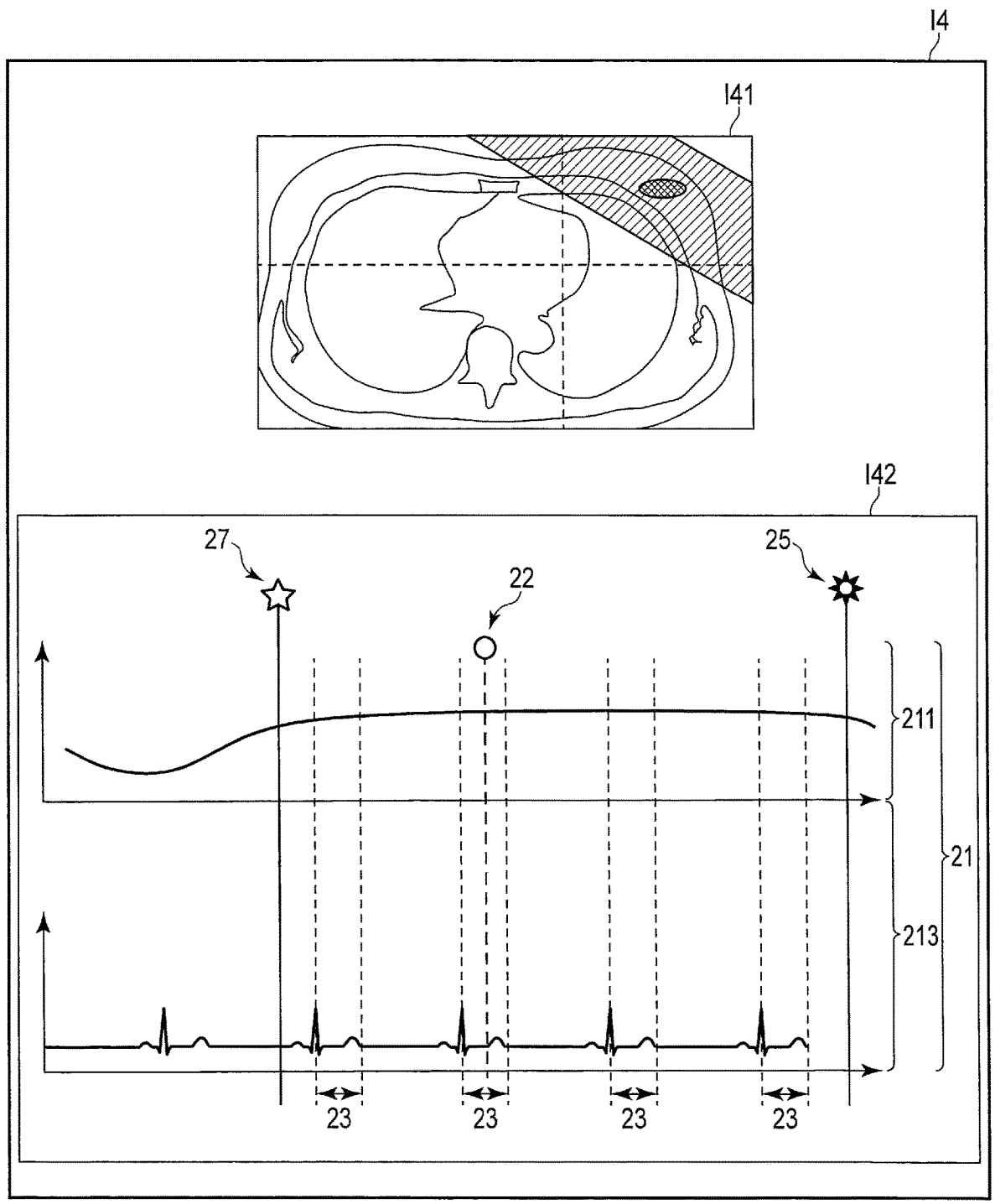
F I G. 10

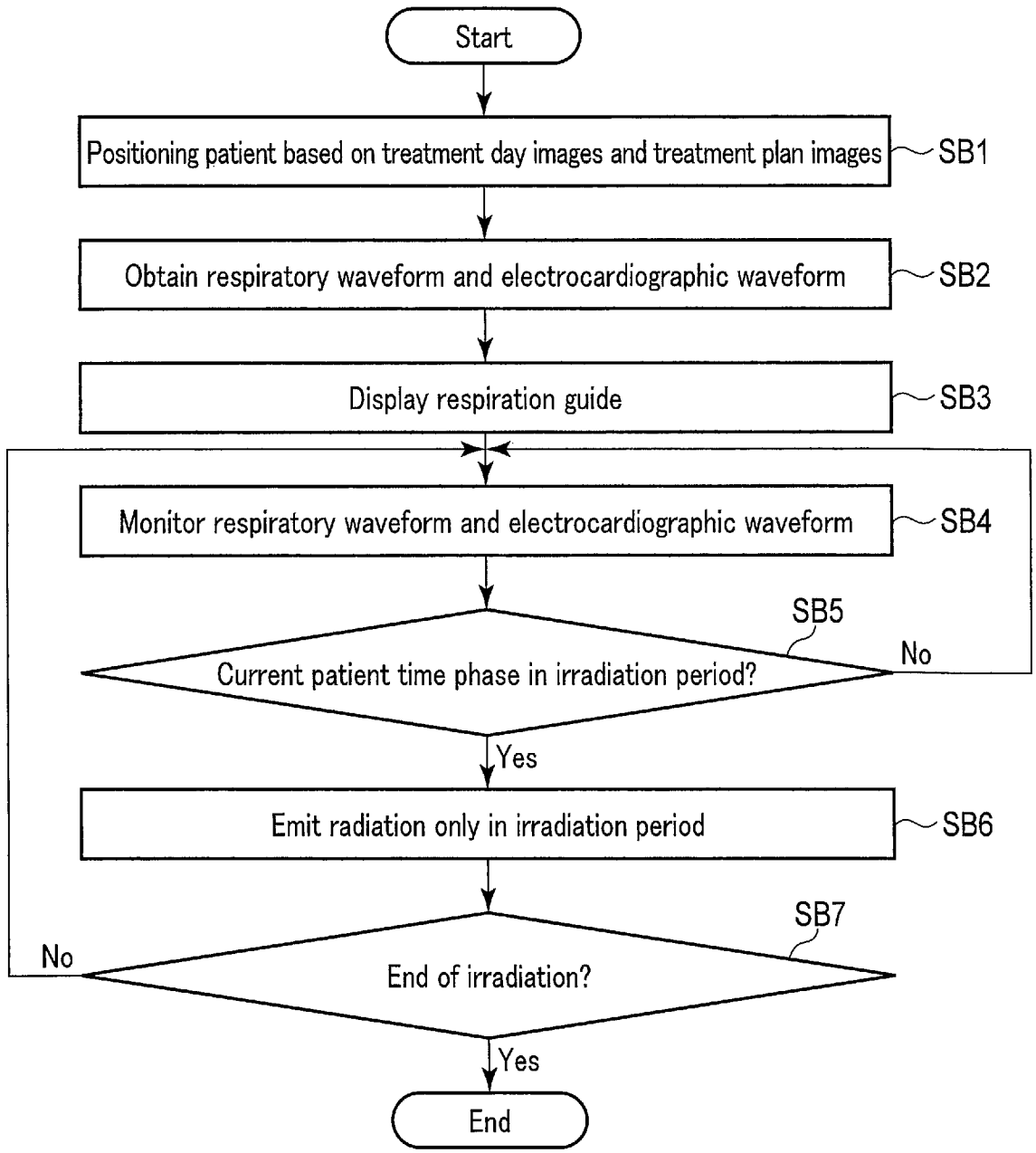
F I G. 12

RADIATION TREATMENT PLANNING APPARATUS AND RADIATION TREATMENT APPARATUS

CROSS-REFERENCE TO RELATED APPLICATIONS

This application is based upon and claims the benefit of priority from the prior Japanese Patent Application No. 2020-008528, filed Jan. 22, 2020 the entire contents of which are incorporated herein by reference.

FIELD

Embodiments described herein relate generally to a radiation treatment planning apparatus and a radiation treatment apparatus.

BACKGROUND

One of radiation treatment techniques is an irradiation technique of avoiding an organ at risk such as the heart by respiratory control of a patient such as DIBH (Deep Inspiration Breath Hold) at the time of radiation treatment to the chest, especially the left chest. However, this technique does not consider the motion of the heart. When radiation passes through part of the heart to irradiate the heart at the time of dilatation, the exposure of the heart increases. The exposure of the heart seriously affects the prognosis such as a toxicity of the patient, and thus needs to be minimized. In irradiation causing the exposure of part of the heart, the dose distribution may change depending on the motion of the heart and the heart may be irradiated with a dose distribution different from one set by a treatment plan.

BRIEF DESCRIPTION OF THE DRAWINGS

FIG. 10 is a view showing an example of the display screen of the irradiation time phase;

FIG. 12 is a flowchart showing a sequence of radiation treatment by a processing circuitry shown in FIG. 11;

DETAILED DESCRIPTION

In general, according to one embodiment, a radiation treatment planning apparatus includes a processing circuitry. The processing circuitry obtains time-series medical images. The processing circuitry specifies the first time phase in which radiation irradiation is performed and the second time phase in which no radiation irradiation is performed, in a period corresponding to the time-series medical images based on the positional relationship between a treatment target region and at-risk region of a patient included in the time-series medical images. The processing circuitry generates a treatment plan based on a medical image of the specified first time phase.

A radiation treatment planning apparatus and a radiation treatment apparatus according to the embodiment will be described below with reference to the drawings.

Figure 1:
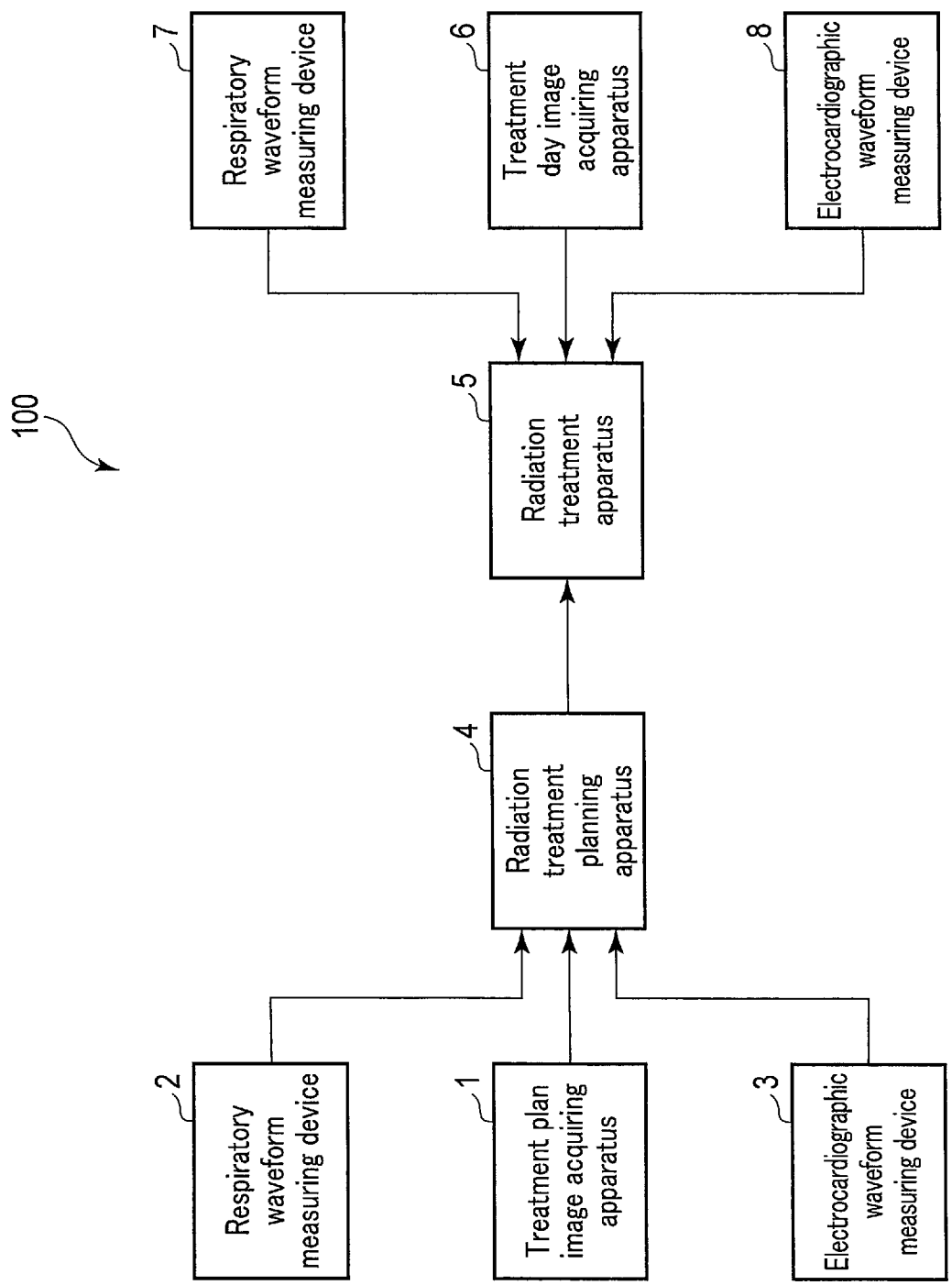
FIG. 1 is a block diagram showing an example of the arrangement of a radiation treatment system.

FIG. 1 is a block diagram showing an example of the arrangement of a radiation treatment system 100. As shown in FIG. 1, the radiation treatment system 100 includes a treatment plan image acquiring apparatus 1, a respiratory waveform measuring device 2, an electrocardiographic waveform measuring device 3, a radiation treatment planning apparatus 4, a radiation treatment apparatus 5, a treatment day image acquiring apparatus 6, a respiratory waveform measuring device 7, and an electrocardiographic waveform measuring device 8.

The treatment plan image acquiring apparatus 1 performs medical photographing of a treatment target patient and generates medical images used for a treatment plan. The medical image used for a treatment plan will be called a treatment plan image. The treatment plan image may be a two-dimensional image formed from a two-dimensional array of pixels or a three-dimensional image formed from a three-dimensional array of voxels. The treatment plan image acquiring apparatus 1 may be any modality apparatus capable of generating a treatment plan image. The modality apparatus is, for example, an X-ray computed tomography apparatus, a magnetic resonance imaging apparatus, a cone-beam CT apparatus, or a nuclear-medical diagnostic apparatus. The treatment plan image acquiring apparatus 1 performs moving image photographing of the treatment target patient and generates treatment plan images of a plurality of time phases. The treatment plan images of a plurality of time phases are transmitted to the radiation treatment planning apparatus 4.

The respiratory waveform measuring device 2 is a measuring device that measures a physical quantity changing with the respiration of the patient. The respiratory waveform measuring device 2 is, for example, a mechanical position measuring device, laser measuring device, or radar measuring device that measures the position (to be referred to as respiratory level hereinafter) of a region such as the chest changing in position with respiration. The respiratory waveform measuring device 2 may be a ventilation volume meter that measures a ventilation volume, or an expiration volume meter that measures an expiration volume. The respiratory waveform measuring device 2 measures a respiratory waveform changing with the respiration of the treatment target patient during medical photographing by the treatment plan image acquiring apparatus 1. The respiratory waveform is transmitted to the radiation treatment planning apparatus 4.

The electrocardiographic waveform measuring device 3 is a measuring device that measures a physical quantity changing with the pulsation of the heart of the patient. The electrocardiographic waveform measuring device 3 is, for example, an electrocardiograph that measures a cardiac potential. The electrocardiographic waveform measuring device 3 may also be a pulsometer that measures a pulse pressure, a sphygmomanometer that measures a blood pressure, or a laser measuring device or radar measuring device that measures the position of the heart. The electrocardiographic waveform measuring device 3 measures an electrocardiographic waveform changing with the pulsation of the heart of the treatment target patient during medical photographing by the treatment plan image acquiring apparatus 1. The electrocardiographic waveform is transmitted to the radiation treatment planning apparatus 4.

The radiation treatment planning apparatus 4 is a computer that generates a treatment plan about the treatment target patient. The radiation treatment planning apparatus 4 generates a treatment plan based on the treatment plan images of a plurality of time phases, the respiratory waveform, and the electrocardiographic waveform. The treatment plan is transmitted to the radiation treatment apparatus 5.

The radiation treatment apparatus 5 is an apparatus that irradiates the patient with radiation for the purpose of treatment. The radiation treatment apparatus 5 is, for example, an X-ray treatment apparatus that emits X-rays, a particle beam treatment apparatus that emits a particle beam, or a heavy particle beam treatment apparatus that emits a heavy particle beam. The radiation treatment apparatus 5 irradiates the patient with radiation gated with the electrocardiographic waveform from the electrocardiographic waveform measuring device 8 and the respiratory waveform from the respiratory waveform measuring device 7 in accordance with the treatment plan generated by the radiation treatment planning apparatus 4. The radiation irradiation gated with the electrocardiographic waveform and the respiratory waveform will be called electrocardiogram/respiration-gated irradiation.

On the day of radiation treatment, the treatment day image acquiring apparatus 6 performs medical photographing of the treatment target patient and generates medical images. The medical image generated by the treatment day image acquiring apparatus 6 will be called a treatment day image. The radiation treatment day is specially a time immediately before or during radiation irradiation. The treatment day image is used for alignment with a treatment plan image. The treatment day image may be a two-dimensional image formed from a two-dimensional array of pixels or a three-dimensional image formed from a three-dimensional array of voxels. Similar to the treatment plan image acquiring apparatus 1, the treatment day image acquiring apparatus 6 may be any modality apparatus capable of generating a treatment day image. The treatment day image is transmitted to the radiation treatment apparatus 5.

Similar to the respiratory waveform measuring device 2, the respiratory waveform measuring device 7 is a measuring device that measures a physical quantity changing with the respiration of the patient. The respiratory waveform measuring device 7 measures a respiratory waveform changing with the respiration of the treatment target patient at the time of radiation treatment. The respiratory waveform is used for electrocardiogram/respiration-gated irradiation by the radiation treatment apparatus 5. The respiratory waveform is transmitted to the radiation treatment apparatus 5.

Similar to the electrocardiographic waveform measuring device 3, the electrocardiographic waveform measuring device 8 is a measuring device that measures a physical quantity changing with the pulsation of the heart of the patient. The electrocardiographic waveform measuring device 8 measures an electrocardiographic waveform changing with the pulsation of the heart of the treatment target patient at the time of radiation treatment. The electrocardiographic waveform is used for electrocardiogram/respiration-gated irradiation by the radiation treatment apparatus 5. The electrocardiographic waveform is transmitted to the radiation treatment apparatus 5.

Next, the radiation treatment planning apparatus 4 will be described in detail.

Figure 2:
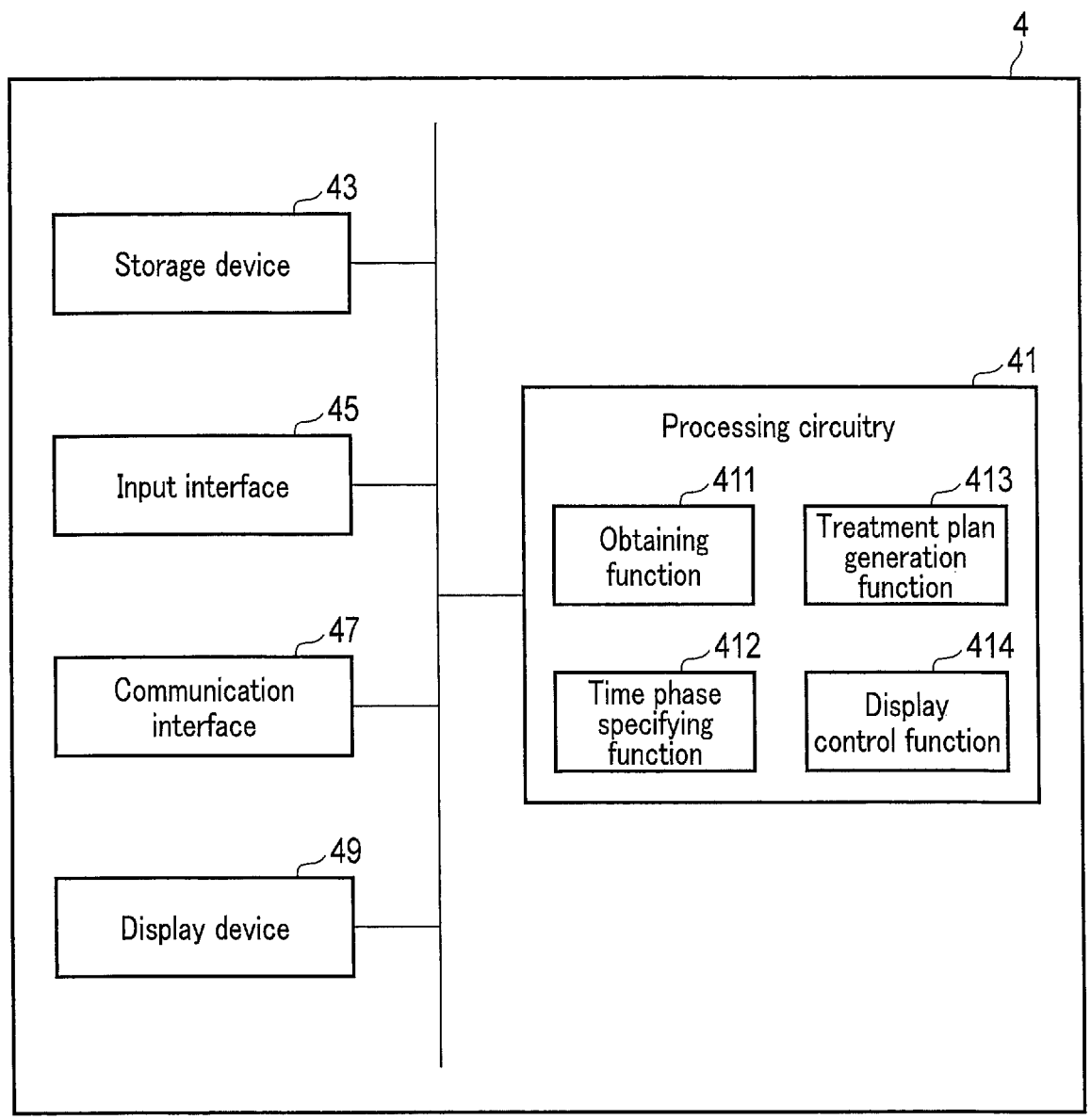
FIG. 2 is a block diagram showing the arrangement of a radiation treatment planning apparatus shown in FIG. 1.

FIG. 2 is a block diagram showing the arrangement of the radiation treatment planning apparatus 4. As shown in FIG. 2, the radiation treatment planning apparatus 4 includes a processing circuitry 41, a storage device 43, an input interface 45, a communication interface 47, and a display device 49. The processing circuitry 41 is an example of a processing unit, the storage device 43 is an example of a storage unit, the input interface 45 is an example of an input unit, the communication interface 47 is an example of a communication unit, and the display device 49 is an example of a display unit.

The processing circuitry 41 includes a processor. The processor activates various programs installed in the storage device 43 and the like, implementing an obtaining function 411, a time phase specifying function 412, a treatment plan generation function 413, and a display control function 414. The functions 411 to 414 are implemented not only by the single processing circuitry 41, but also by combining a plurality of independent processors into a processing circuitry and executing programs by the respective processors.

By the implementation of the obtaining function 411, the processing circuitry 41 obtains various kinds of information. For example, the processing circuitry 41 obtains treatment plan images of a patient about a plurality of time phases that are generated by the treatment plan image acquiring apparatus 1. More specifically, the processing circuitry 41 obtains time-series treatment plan images about the patient. The processing circuitry 41 obtains the respiratory waveform of the patient measured by the respiratory waveform measuring device 2, and the electrocardiographic waveform of the patient measured by the electrocardiogram measuring device 3. Note that the form of obtaining is not limited to direct form from the treatment plan image acquiring apparatus 1 or the like, and information received from the treatment plan image acquiring apparatus 1 or the like may be stored in the storage device 43 and obtained from the storage device 43.

By the implementation of the time phase specifying function 412, the processing circuitry 41 specifies, from a plurality of time phases, a specific time phase that satisfies a distance standard about the distance between an at-risk region and a treatment target region or an irradiation path passing through the treatment target region that are included in a treatment plan image, and/or a dose standard about an irradiation dose applied to the at-risk region. The treatment target region is an anatomical region including a tumor serving as a radiation irradiation target. The at-risk region is an anatomical region that is near the treatment target region and highly sensitive to radiation. In other words, the processing circuitry 41 specifies the first time phase in which radiation irradiation is performed and the second time phase in which no radiation irradiation is performed, in a period corresponding to time-series medical images based on the positional relationship between the treatment target region and at-risk region of the patient included in the time-series medical images. The first time phase is a specific time phase that satisfies the distance standard and/or the dose standard, and the second time phase is a specific time phase that does not satisfy the distance standard and/or the dose standard. For example, the processing circuitry 41 specifies the first and second time phases based on the distance between the treatment target region and the at-risk region. As another example, the processing circuitry 41 specifies the first and second time phases based on the distance between the at-risk region and the irradiation path of radiation passing through the treatment target region. As still another example, the processing circuitry specifies the first and second time phases based on the amount of overlap between the at-risk region and the irradiation path of radiation passing through the treatment target region. As still another example, the processing circuitry specifies the first and second time phases based an irradiation dose to the at-risk region obtained from radiation passing through the treatment target region.

By the implementation of the treatment plan generation function 413, the processing circuitry 41 generates a treatment plan based on a medical image about the specific time phase.

By the implementation of the display control function 414, the processing circuitry 41 displays various kinds of information via the display device 49. For example, the processing circuitry 41 displays a treatment plan image, a treatment plan screen, a treatment plan, and the like.

The storage device 43 is a storage device such as a ROM (Read Only Memory), RAM (Random Access Memory), HDD (Hard Disk Drive), SSD (Solid State Drive), or integrated circuitry storage device that stores various kinds of information. The storage device 43 stores, for example, medical images of a plurality of time phases, an electrocardiographic waveform, and a respiratory waveform that are obtained by the obtaining function 411. The storage device 43 may be a portable storage medium such as a CD (Compact Disc), DVD (Digital Versatile Disc), or flash memory, or a driver that reads and writes various kinds of information from and in a semiconductor memory element or the like, other than the above-mentioned storage device. The storage device 43 may be installed in another computer connected to the radiation treatment planning apparatus 4 via a network.

The input interface 45 accepts various input operations from the user, converts the accepted input operations into electrical signals, and outputs them to the processing circuitry 41. More specifically, the input interface 45 is connected to an input device such as a mouse, keyboard, trackball, switches, buttons, joystick, touch pad, or touch panel display. The input interface 45 may be a voice input device using a voice signal from an input device such as a microphone that collects a voice. The input interface 45 may be a contactless input circuitry using an optical sensor. The input interface 45 outputs, to the processing circuitry 41, an electrical signal corresponding to an input operation to the input device. An input device connected to the input interface 45 may be an input device provided in another computer connected via a network or the like.

The communication interface 47 is an interface for performing information communication with the treatment plan image acquiring apparatus 1, the respiratory waveform measuring device 2, the electrocardiographic waveform measuring device 3, and the radiation treatment apparatus 5.

The display device 49 displays various kinds of information according to the display control function 414 of the processing circuitry 41. The display device 49 can be, for example, a LCD (Liquid Crystal Display), CRT (Cathode Ray Tube) display, OELD (Organic Electro Luminescence Display), plasma display, or another arbitrary display. The display device 49 may be a projector.

Next, an example of an operation of generating a treatment plan by the processing circuitry 41 of the radiation treatment planning apparatus 4 will be explained.

Figure 3:
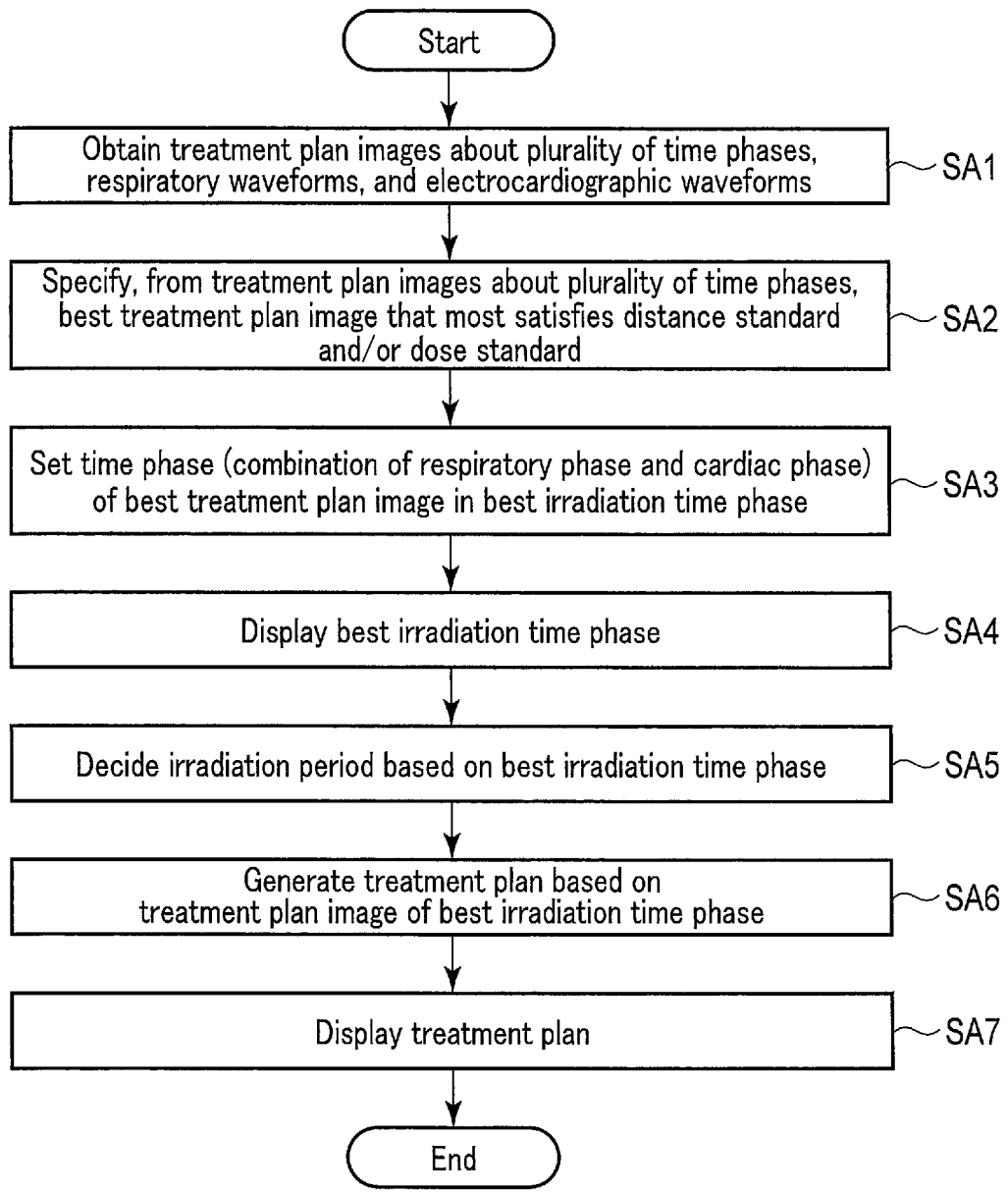
FIG. 3 is a flowchart showing a sequence of generating a treatment plan by a processing circuitry in FIG. 2.

FIG. 3 is a flowchart showing a sequence of generating a treatment plan by the processing circuitry 41. At the start in FIG. 3, the treatment plan image acquiring apparatus 1 has already performed medical moving image photographing of a treatment target patient and generated treatment plan images of a plurality of time phases. At the time of medical moving image photographing, the respiratory waveform measuring device 2 has generated the respiratory waveform of the treatment target patient, and the electrocardiographic waveform measuring device 3 has generated the electrocardiographic waveform of the treatment target patient. The treatment plan image is a three-dimensional medical image.

In the following description, the treatment target region is a tumor in the left chest, and the at-risk region is the heart or its blood vessels. The shape of the left chest, that of the heart or its blood vessels, and the positional relationship between the left chest and the heart or its blood vessels change intricately in synchronization with the respiratory motion and the pulsation of the heart. In consideration of both the respiratory time phase and the cardiac phase, the processing circuitry 41 specifies, from a plurality of time phases, a specific time phase in which the treatment target region and the at-risk region are relatively spaced apart from each other. The processing circuitry 41 generates a treatment plan based on a treatment plan image of the specific time phase.

As shown in FIG. 3, the processing circuitry 41 first obtains treatment plan images about a plurality of time phases, respiratory waveforms, and electrocardiographic waveforms by the implementation of the obtaining function 411 (step SA1). The treatment plan images about a plurality of time phases are associated with respiratory waveforms and electrocardiographic waveforms. The time phase of each treatment plan image is defined by a combination of a cardiac phase associated with the pulsation of the heart of the treatment target patient and a respiratory time phase associated with the respiration of the patient. The time phase defined by a combination of the cardiac phase and the respiratory time phase will be called a patient time phase. The treatment plan images about a plurality of time phases are, for example, time-series treatment plan images.

The respiratory waveform is associated with a respiratory time phase regarding the respiration of the treatment target patient. The respiratory waveform is a curve representing a temporal change of the respiratory level. The respiratory level and the respiratory time phase are associated for every time. The respiratory time phase is divided into an expiratory phase serving as a period in which the respiratory level of the respiratory waveform is equal to or lower than a predetermined value, and an inspiratory phase serving as a period in which the respiratory level is equal to or higher than the predetermined value. The respiratory time phase may be defined by time phase periods as described above, or represented by a percentage when the time interval of the start time or end time of the inspiratory phase or expiratory phase is defined as 100%.

The electrocardiographic waveform is associated with a cardiac phase regarding the pulsation of the heart of the treatment target patient. The electrocardiographic waveform is a curve representing a temporal change of the cardiac potential. The cardiac potential and the cardiac phase are associated for every time. The cardiac phase is divided into a diastolic phase and a contraction phase. The diastolic phase is divided into an isovolumetric relaxation phase, an inflow phase, and an atrial contraction phase. The contraction phase is divided into an isovolumetric contraction phase and an ejection phase. The cardiac phase may be defined by time phase periods as described above, or represented by a percentage when the time interval between specific feature waves (for example, R waves) is defined as 100%.

Note that the reference value of the respiratory rate is 16 to 20 breaths/min, that is, 3.75 to 3.0 sec/breath. The reference value of the heart beat (pulse) is 60 to 100 beats/min, that is, 1 to 0.6 sec/beat. That is, the electrocardiogram has about ¼ to ⅕ cycle of the respiratory waveform.

After step SA1, the processing circuitry 41 specifies, from the treatment plan images about a plurality of time phases by the implementation of the time phase specifying function 412, a treatment plan image (to be referred to as a best treatment plan image hereinafter) that most satisfies the distance standard and/or the dose standard (step SA2). The distance standard is a standard about the distance between a treatment target region included in the treatment plan image and an at-risk region or irradiation path. More specifically, the distance standard is defined by a standard (first distance standard) in which the distance between the at-risk region and an irradiation path passing through the treatment target region is equal to or larger than a predetermined value, a standard (second distance standard) in which the distance between the treatment target region and the at-risk region is equal to or larger than a predetermined value, and/or a standard (third distance standard) in which the volume or area of overlap between the at-risk region and the irradiation path is equal to or smaller than a predetermined value. The dose standard is a standard about an irradiation dose applied to the at-risk region. More specifically, the dose standard is defined by a standard in which the irradiation dose applied to the at-risk region is equal to or smaller than a predetermined value. In the best treatment plan image, the at-risk region and the treatment target region are considered to be relatively spaced apart from each other.

Figure 4:
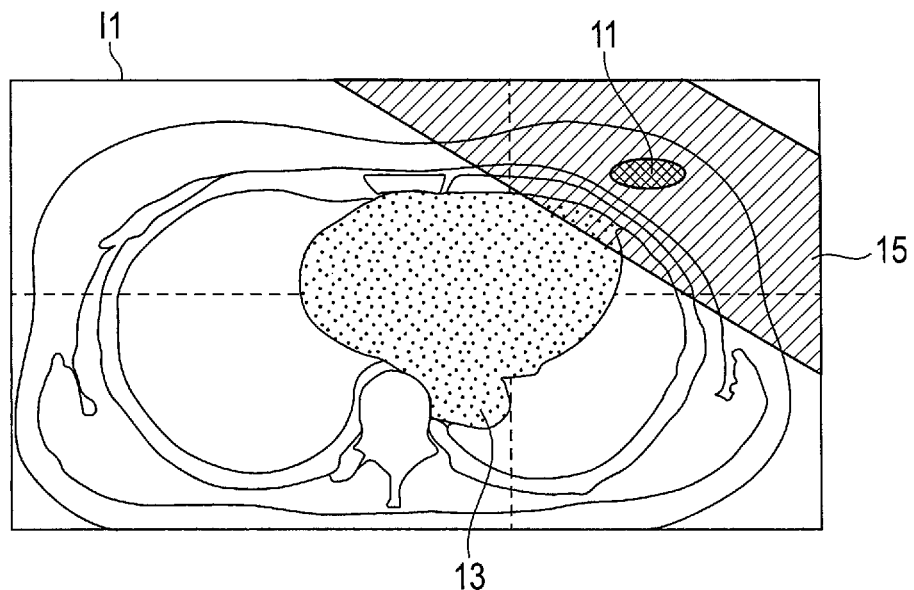
FIG. 4 is a view showing an example of a treatment plan image in the expiratory phase and the diastolic phase.
Figure 5:
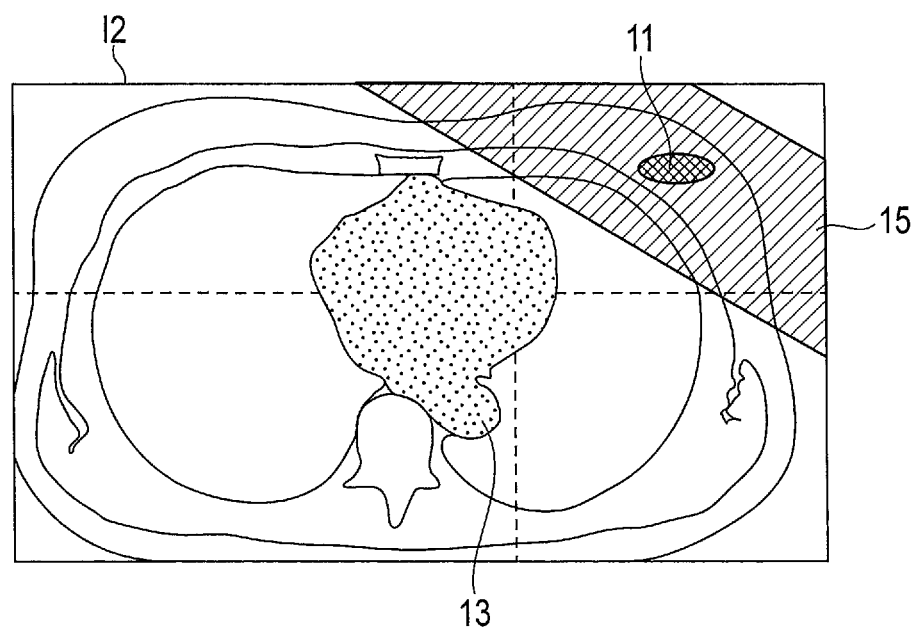
FIG. 5 is a view showing an example of a treatment plan image in the inspiratory phase and the contraction phase.

The specification of the best treatment plan image using the distance standard and the dose standard will be described with reference to FIGS. 4 and 5. FIG. 4 is a view showing an example of a treatment plan image I1 in the expiratory phase and the diastolic phase. FIG. 5 is a view showing an example of a treatment plan image I2 in the inspiratory phase and the contraction phase.

As shown in FIGS. 4 and 5, each of the treatment plan images I1 and I2 includes an image region (to be referred to as a tumor region hereinafter) 11 regarding the tumor in the left chest serving as the treatment target region, and an image region (to be referred to as a heart region hereinafter) 13 regarding the heart serving as the at-risk region. The processing circuitry 41 performs image processing on the treatment plan images I1 and I2 for the respective time phases, and extracts the tumor region 11 and the heart region 13. The image processing can be region extraction using threshold processing, texture analysis, machine learning, and anatomical feature point detection. Region extraction may be performed according to region designation by the user via the input interface 45.

In the first distance standard, the processing circuitry 41 first sets, in the treatment plan images I1 and I2, an irradiation path 15 that passes through the tumor region 11. Then, the processing circuitry 41 calculates a distance between the irradiation path 15 and the heart region 13. The definition of the distance is not particularly limited. For example, the distance is defined by the shortest distance between the irradiation path 15 and the heart region 13.

Figure 6:
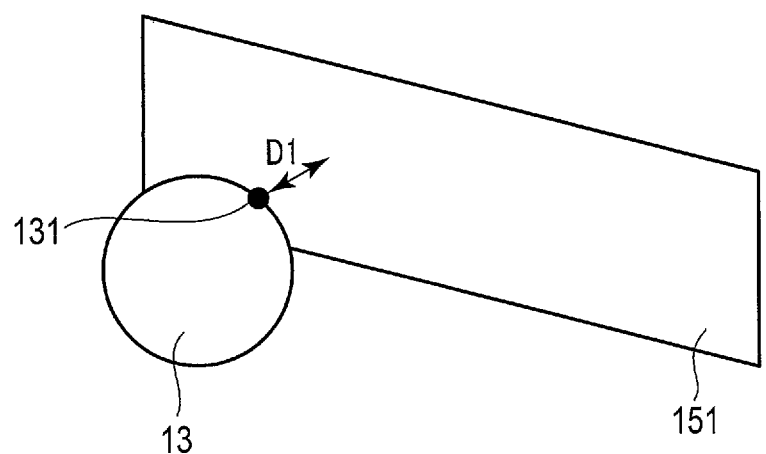
FIG. 6 is a view showing the shortest distance between an irradiation path and a heart region.

FIG. 6 is a view showing the shortest distance between the irradiation path 15 and the heart region 13. As shown in FIG. 6, the processing circuitry 41 first specifies a plane 151 on the heart region 13 side out of the outer plane of the irradiation path 15. The outer plane or the plane 151 is defined by a plane connecting corner points included in the irradiation path 15 or an aggregate of polygons connecting adjacent lattice points forming the irradiation path 15. Then, the processing circuitry 41 calculates normals to the respective voxels of the surface of the heart region 13 that pass through the plane 151. As for the plane 151, the processing circuitry 41 sets the length of the shortest normal among the normals as the shortest distance between the irradiation path 15 and the heart region 13.

Note that the distance between the irradiation path 15 and the heart region 13 is not limited to the shortest distance and may be defined by the distance between the representative point of the irradiation path 15 and that of the heart region 13. The representative point is defined by the center point or barycenter point of the irradiation path 15 or heart region 13 or the like. The distance between the irradiation path 15 and the heart region 13 may be defined by any other way.

After calculating the distance between the irradiation path 15 and the heart region 13, the processing circuitry 41 compares the calculated distance with a predetermined value. The predetermined value may be an arbitrary value. For example, the predetermined value is preferably set to be 0 or more. When the overlap between the irradiation path 15 and the heart region 13 is permitted, the predetermined value may be smaller than 0. If the distance is equal to or larger than the predetermined value, the processing circuitry 41 determines that the treatment plan image satisfies the first distance standard. If the distance is equal to or smaller than the predetermined value, the processing circuitry 41 determines that the treatment plan image does not satisfy the first distance standard.

In the case of the second distance standard, the processing circuitry 41 first calculates a distance between the tumor region 11 and the heart region 13. The definition of the distance is not particularly limited. For example, the distance is defined by the shortest distance between the tumor region 11 and the heart region 13. For example, the distance between the tumor region 11 and the heart region 13 may be defined by the distance between the representative point of the tumor region 11 and that of the heart region 13. The representative point is defined by the center point or barycenter point of the tumor region 11 or heart region 13 or the like. The distance between the tumor region 11 and the heart region 13 may be defined by any other way.

After calculating the distance between the tumor region 11 and the heart region 13, the processing circuitry 41 compares the calculated distance with a predetermined value. The predetermined value may be an arbitrary value. For example, when the irradiation path 15 is set in the treatment plan images I1 and I2, the predetermined value is preferably set to be a distance at which the irradiation path 15 is not superposed on the heart region 13. Note that the irradiation path 15 is set to pass through the tumor region 11. If the distance is equal to or larger than the predetermined value, the processing circuitry 41 determines that the treatment plan image satisfies the second distance standard. If the distance is equal to or smaller than the predetermined value, the processing circuitry 41 determines that the treatment plan image does not satisfy the second distance standard.

In the case of the third distance standard, the processing circuitry 41 first sets the irradiation path 15 in the treatment plan images I1 and I2 so that the irradiation path 15 passes through the tumor region 11. Then, the processing circuitry 41 calculates a volume of overlap between the irradiation path 15 and the heart region 13. The volume of overlap is defined by, for example, the number of voxels of an image region where the irradiation path 15 and the heart region 13 overlap each other. Thereafter, the processing circuitry 41 compares the volume of overlap with a predetermined value. The predetermined value may be an arbitrary value. For example, the predetermined value is set to be a volume value at which the application of the dose of radiation is permitted. If the volume of overlap is equal to or smaller than the predetermined value, the processing circuitry 41 determines that the treatment plan image satisfies the third distance standard. If the volume of overlap is equal to or larger than the predetermined value, the processing circuitry 41 determines that the treatment plan image does not satisfy the third distance standard.

The determination of the distance standard has been described above. In step SA2, the processing circuitry 41 may specify a treatment plan image that satisfies one of the first, second, and third distance standards, or specify a treatment plan image that satisfies two or more of the first, second, and third distance standards.

In the case of the dose standard, the processing circuitry 41 sets the irradiation path 15 in the treatment plan images I1 and I2, and calculates an irradiation dose applied to the heart region 13. Then, the processing circuitry 41 compares the irradiation dose with a predetermined value. The predetermined value may be an arbitrary value. For example, the predetermined value is set to be a dose value at which the application of the dose of radiation is permitted. If the irradiation dose is equal to or smaller than the predetermined value, the processing circuitry 41 determines that the treatment plan image satisfies the dose standard. If the irradiation dose is equal to or larger than the predetermined value, the processing circuitry 41 determines that the treatment plan image does not satisfy the dose standard.

The determination of the dose standard has been described above. In step SA2, the processing circuitry 41 may specify a treatment plan image that satisfies either the distance standard or the dose standard, or specify a treatment plan image that satisfies both the distance standard and the dose standard. In this case, a treatment plan image that satisfies the dose standard and at least one of the first, second, and third distance standards is specified.

When only one treatment plan image is specified in step SA2, it is set as the best treatment plan image. When two or more treatment plan images are specified, a treatment plan image that most satisfies the distance standard and/or the dose standard is set as the best treatment plan image.

Step SA2 is performed for, for example, all treatment plan images about a plurality of time phases in one respiratory cycle. In some cases, two or more treatment plan images may be specified in step SA2 as treatment plan images that satisfy the distance standard and/or the dose standard. Step SA3 may also be performed for a plurality of treatment plan images about a plurality of time phases in a period shorter than one respiratory cycle, or for a plurality of treatment plan images about a plurality of time phases in a period longer than one respiratory cycle.

After step SA2, the processing circuitry 41 sets the time phase of the best treatment plan image specified in step SA2 in the best irradiation time phase by the implementation of the time phase specifying function 412 (step SA3). The best irradiation time phase is a time phase used in the treatment plan. The best irradiation time phase is defined by a combination of the respiratory time phase and the cardiac phase. For example, in step SA3, the processing circuitry 41 specifies, from supplementary information or the like, the photographing time of the best treatment plan image specified in step SA2, and specifies a respiratory waveform and electrocardiographic waveform associated with the treatment plan image. Then, the processing circuitry 41 specifies the respiratory time phase of the respiratory waveform and the cardiac phase of the electrocardiographic waveform that correspond to the specified photographing time. A combination of the respiratory time phase and the cardiac phase is set in the best irradiation time phase.

After step SA3, the processing circuitry 41 displays the best irradiation time phase set in step SA3 by the implementation of the display control function 414 (step SA4). In step SA4, the processing circuitry 41 displays the display screen of the irradiation time phase on the display device 49.

Figure 7:
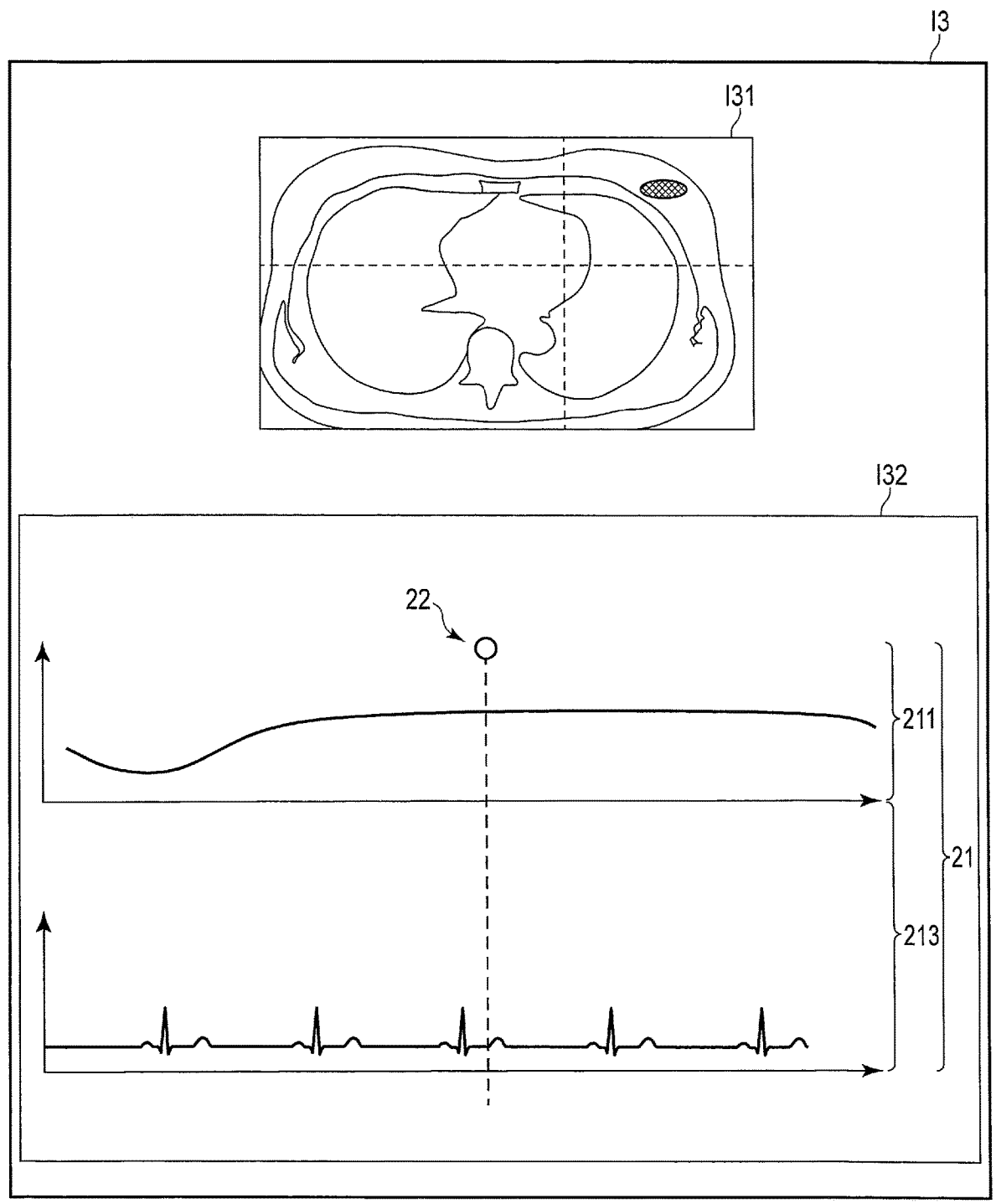
FIG. 7 is a view showing an example of the display screen of an irradiation time phase.

FIG. 7 is a view showing an example of a display screen 13 of the irradiation time phase. As shown in FIG. 7, the display screen 13 displays a best treatment plan image I31 and a waveform display field I32. The best treatment plan image I31 satisfies the distance standard and/or the dose standard, so the treatment target region and the at-risk region are rendered at a distance.

As shown in FIG. 7, a graph 21 in which a respiratory waveform 211 and an electrocardiographic waveform 213 obtained in step SAL are represented on the same time axis is displayed in the waveform display field I32. In FIG. 7, the respiratory waveform 211 under deep inspiration breath hold is displayed on the upper stage of the waveform display field I32. That is, the same positions of the respiratory waveform 211 and electrocardiographic waveform 213 on the abscissa correspond to the same time. From this display, the user can clearly grasp the correspondence between the respiratory time phase in the respiratory waveform 211 and the cardiac phase in the electrocardiographic waveform 213.

As shown in FIG. 7, a mark 22 indicating the patient time phase of the best treatment plan image I31, that is, the best irradiation time phase is displayed in the waveform display field I32. The mark 22 indicates the time corresponding to the best irradiation time phase in the respiratory waveform 211 and the electrocardiographic waveform 213. The user checks the time phase indicated by the mark 22 in the respiratory waveform and the electrocardiographic waveform, and can visually grasp a respiratory time phase period, cardiac phase period, and the like to which the best irradiation time phase belongs. The mark 22 and the best treatment plan image I31 can be displayed synchronously. For example, the user may slide the display position of the mark 22 along the time phase axis of the respiratory waveform and electrocardiographic waveform via the input interface 45, and display a treatment plan image corresponding to a patient time phase indicated by the mark 22 as the best treatment plan image I31.

After step SA4, the processing circuitry 41 decides an irradiation period based on the best irradiation time phase by the implementation of the time phase specifying function 412 (step SA5). The irradiation period is a time period in which the radiation treatment apparatus 5 emits radiation. The irradiation period is set in, for example, a predetermined time phase period including the best irradiation time phase. A respiratory time phase period corresponding to the respiratory time phase [%] and a cardiac phase period corresponding to the cardiac phase [%] in the best irradiation time phase are specified, and a combination of the respiratory time phase period and the cardiac phase period is set in the irradiation period.

Figure 8:
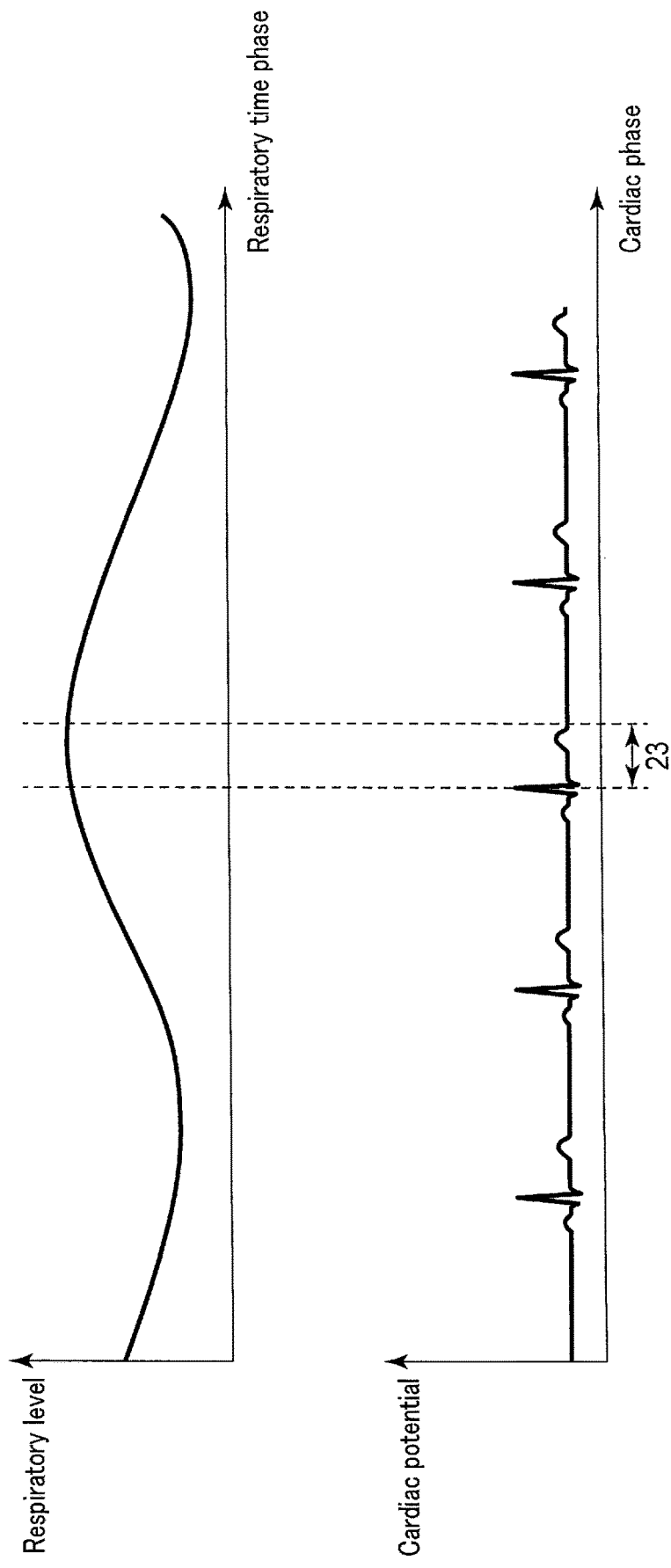
FIG. 8 is a graph showing a respiratory waveform, an electrocardiographic waveform, and an irradiation time phase under free breathing.
Figure 9:
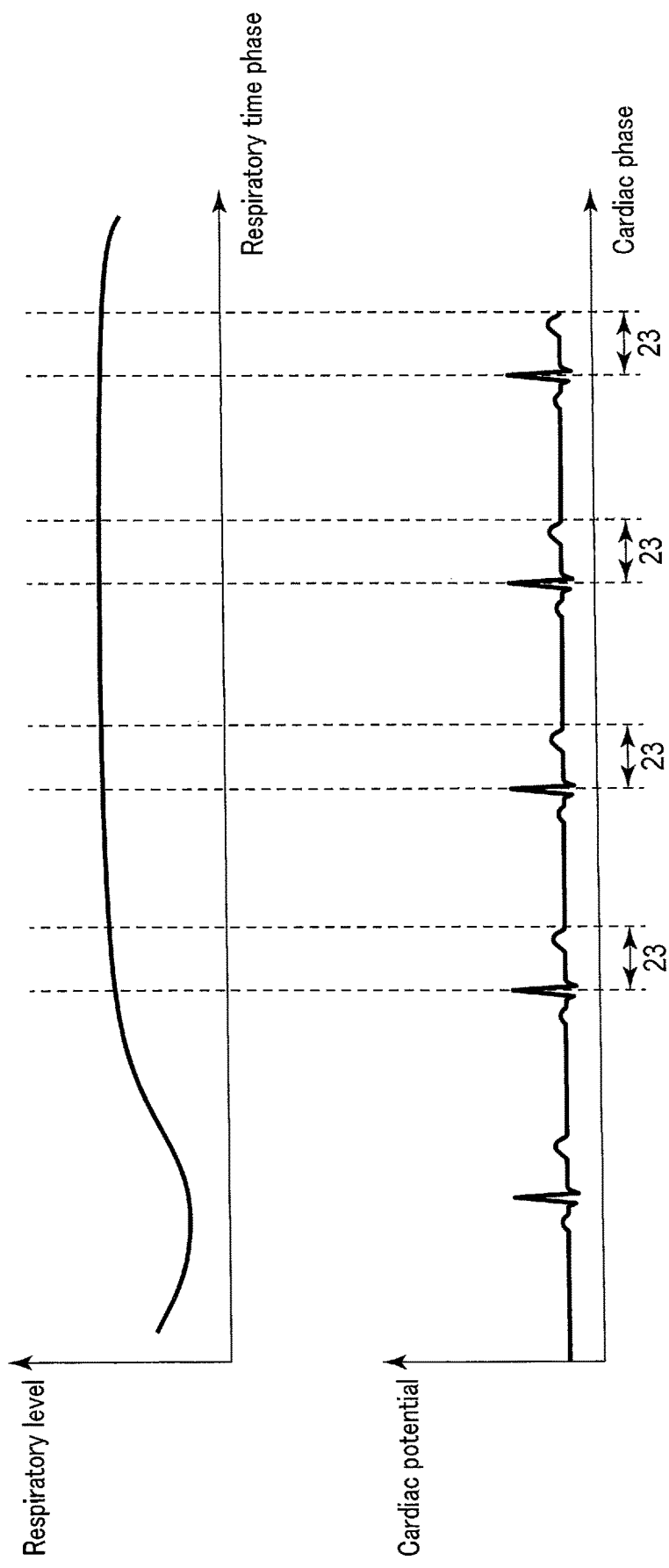
FIG. 9 is a graph showing a respiratory waveform, an electrocardiographic waveform, and an irradiation time phase under deep inspiration breath hold.

FIG. 8 is a graph showing a respiratory waveform, an electrocardiographic waveform, and an irradiation period under free breathing. FIG. 9 is a graph showing a respiratory waveform, an electrocardiographic waveform, and an irradiation period under deep inspiration breath hold. In FIGS. 8 and 9, a respiratory time phase "inspiratory phase" and a cardiac phase "contraction phase" are set in an irradiation period 23. The respiratory time phase hardly changes under deep inspiration breath hold, so the total time of the irradiation period 23 in one respiratory cycle under deep inspiration breath hold tends to be longer than the total time in one respiratory cycle under free breathing. A time phase period excluding the irradiation period 23 in a period corresponding to time-series treatment plan images is set in a non-irradiation period in which no radiation is emitted.

Note that a time phase that satisfies both the distance standard and the dose standard may be set in the irradiation period in step SA2. For example, when a time phase determined to satisfy both the distance standard and the dose standard spans time-series time phases, the time-series time phases are preferably set in the irradiation period. At this time, when the time phase that satisfies both the distance standard and the dose standard includes the first time phase period including the best irradiation time phase set in step SA3 and the second time phase period not including it, only the first time phase period may be set in the irradiation period, or both the first and second time phase periods may be set in the irradiation period.

Although the time phase that satisfies both the distance standard and the dose standard can be set in the irradiation period in the above example, a time phase determined to satisfy either the distance standard or the dose standard may be set in the irradiation period. Time phases determined to satisfy all or some of the distance standards may be set in the irradiation period. A time phase period excluding the irradiation period in a period corresponding to time-series medical images is set as a non-irradiation period.

After step SA5, the processing circuitry 41 generates a treatment plan based on the treatment plan image of the best irradiation time phase by the implementation of the treatment plan generation function 413 (step SA6). Parameters included in the treatment plan are the number of irradiation directions (fields) in the radiation treatment, the irradiation count in each irradiation direction, the irradiation angle, the radiation intensity, the collimator, the dose distribution, and the like. The irradiation count can be calculated by dividing a prospective total applied dose per day by the time length of each irradiation period. The processing circuitry 41 decides various treatment plan parameters based on the positions and shapes of the tumor region and heart region in accordance with the best treatment plan image. At this time, the treatment plan is so generated as to maximize the irradiation dose applied to the tumor region and minimize the irradiation dose applied to the at-risk region.

After step SA6, the processing circuitry 41 displays the treatment plan generated in step SA6 by the implementation of the display control function 414 (step SA7). In step SA7, the processing circuitry 41 displays the display screen of the treatment plan on the display device 49.

FIG. 10 is a view showing an example of a display screen 14 of the treatment plan. As shown in FIG. 10, the display screen 14 displays a best treatment plan image I41 and a waveform display field I42. The dose distribution of the irradiation dose decided in step SA6 may be displayed on the best treatment plan image I41. The graph 21 in which the respiratory waveform and electrocardiographic waveform obtained in step SAL are represented on the same time axis is displayed in the waveform display field I42. Also, the mark 22 indicating the patient time phase of the best treatment plan image I31 is displayed in the graph 21.

As shown in FIG. 10, the irradiation period 23 is displayed emphatically in the graph 21. For example, the irradiation period 23 is displayed in color such as red or yellow, and the remaining period, that is, non-irradiation period is displayed colorlessly. To the contrary, the irradiation period 23 may be displayed colorlessly and the non-irradiation period may be displayed in color such as blue or green. Alternatively, both the irradiation period 23 and the non-irradiation period may be emphasized by color or the like.

As shown in FIG. 10, a breath hold guide for the patient may be displayed in the graph 21. As the breath hold guide, for example, a mark 25 indicating a breath hold release timing is displayed. The user can set an arbitrary timing as the breath hold release timing. As the breath hold guide, for example, a mark 27 indicating a breath hold start timing may be displayed. The user can set an arbitrary timing as the breath hold start timing.

After step SA7, the generation of the treatment plan by the processing circuitry 41 ends.

Note that the sequence of processing regarding the generation of the treatment plan shown in FIG. 3 can be changed variously. For example, in step SA2, a best treatment plan image that satisfies the distance standard and/or the dose standard is specified from a plurality of treatment plan images about a plurality of time phases, but a plurality of treatment plan images that satisfy the distance standard and/or the dose standard may be specified. In this case, the irradiation period is preferably set based on a plurality of time phases corresponding to the respective specified treatment plan images. For example, a period from the start to end time phases of the time phases may be set in the irradiation period, a period shifted by a predetermined time before or after the period from the start to end time phases may be set in the irradiation period, or a period prolonged or shortened from the period from the start to end time phases may be set in the irradiation period.

One or both of the display of the best irradiation time phase in step SA4 and the display of the treatment plan in step SA7 may not be performed.

Data of the treatment plan generated in step SA6 is transmitted to the radiation treatment apparatus 5, and the radiation treatment apparatus 5 performs a radiation treatment according to the treatment plan.

As described above, the radiation treatment planning apparatus 4 includes the processing circuitry 41. The processing circuitry 41 obtains medical images of a patient about a plurality of time phases. The processing circuitry 41 specifies, from the plurality of time phases, a specific time phase that satisfies a distance standard about the distance between an at-risk region included in a medical image and a treatment target region or an irradiation path passing through the treatment target region, and/or a dose standard about an irradiation dose applied to the at-risk region. The processing circuitry 41 generates a treatment plan based on a medical image about the specific time phase.

The above-described arrangement enables generating a treatment plan based on a medical image that satisfies the distance standard and/or the dose standard. Even when the positional relationship between the at-risk region and the treatment target region changes greatly along the respiratory motion and the pulsation of the heart, a treatment plan in which a dose applied to the at-risk region is relatively reduced can be generated.

Next, the radiation treatment apparatus 5 will be described in detail.

Figure 11:
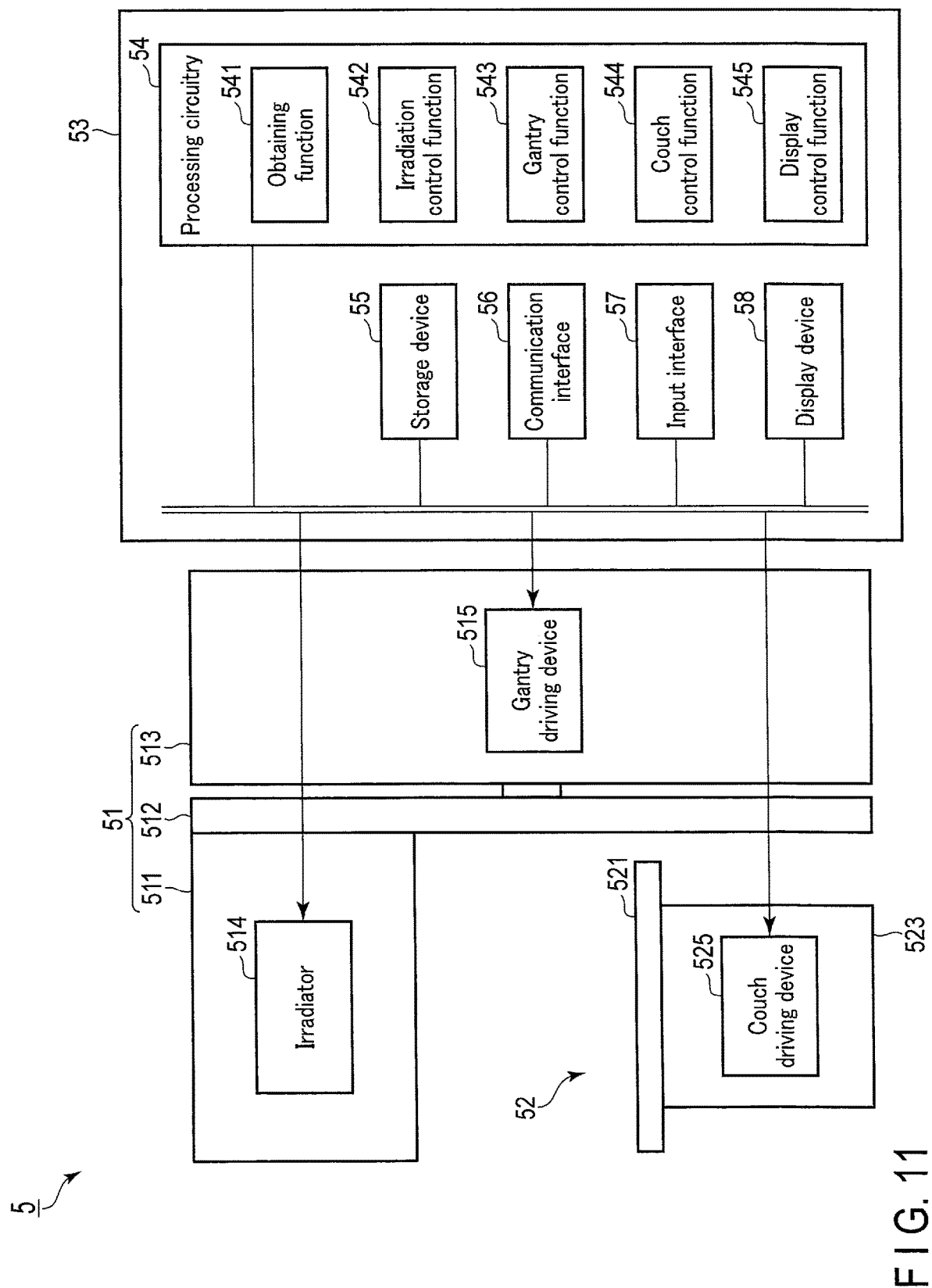
FIG. 11 is a block diagram showing the arrangement of a radiation treatment apparatus shown in FIG. 1.

FIG. 11 is a block diagram showing the arrangement of the radiation treatment apparatus 5. As shown in FIG. 11, the radiation treatment apparatus 5 includes a treatment gantry 51, a treatment couch 52, and a console 53. The treatment gantry 51 includes an irradiation head 511, a rotating portion 512, and a stationary portion 513. The stationary portion 513 is installed on the floor and rotates the rotating portion 512 about a rotating shaft. The irradiation head 511 is attached to the rotating portion 512. The stationary portion 513 incorporates a gantry driving device 515. The gantry driving device 515 receives supply of a control signal from a processing circuitry 54 by a gantry control function 543, and rotates the rotating portion 512 and the irradiation head 511 about the rotating shaft. The irradiation head 511 incorporates an irradiator 514. The irradiator 514 receives supply of a control signal from the processing circuitry 54 by an irradiation control function 542, and emits radiation. The irradiation head 511 and the irradiator 514 are an example of an irradiation unit.

As shown in FIG. 11, the treatment couch 52 includes a treatment top plate 521, a base 523, and a couch driving device 525. A patient is laid on the treatment top plate 521. The treatment top plate 521 is supported by the base 523 so as to move freely. The base 523 is installed on the floor. The base 523 incorporates the couch driving device 525. The couch driving device 525 receives supply of a control signal from a couch control function 544, and moves the treatment top plate 521.

The console 53 includes the processing circuitry 54, a storage device 55, a communication interface 56, an input interface 57, and a display device 58. The processing circuitry 54 is an example of a processing unit, the storage device 55 is an example of a storage unit, the communication interface 56 is an example of a communication unit, the input interface 57 is an example of an input unit, and the display device 58 is an example of a display unit.

The processing circuitry 54 includes a processor. The processor activates various programs installed in the storage device 55 or the like, implementing an obtaining function 541, the irradiation control function 542, the gantry control function 543, the couch control function 544, and a display control function 545. The functions 541 to 545 are implemented by not only the single processing circuitry 54. The functions 541 to 545 may be implemented by combining a plurality of independent processors into a processing circuitry, and executing the programs by the respective processors.

By the implementation of the obtaining function 541, the processing circuitry 54 obtains various kinds of information. More specifically, the processing circuitry 54 obtains a treatment plan that is generated by the radiation treatment planning apparatus 4 and includes an irradiation period defined by a combination of a cardiac phase and a respiratory time phase. The processing circuitry 54 obtains treatment day images generated by the treatment day image acquiring apparatus 6, a respiratory waveform measured by the respiratory waveform measuring device 7, and an electrocardiogram measured by the electrocardiographic waveform measuring device 8. Note that the form of obtaining is not limited to direct from the treatment day image acquiring apparatus 6 or the like, and information received from the treatment day image acquiring apparatus 6 or the like may be stored in the storage device 55 and obtained from the storage device 55.

By the implementation of the irradiation control function 542, the processing circuitry 54 controls the irradiator 514 to emit radiation according to irradiation conditions included in the treatment plan received from the radiation treatment planning apparatus 4. More specifically, the processing circuitry 54 controls the irradiator 514 to emit radiation when the irradiation period includes a patient time phase defined by a respiratory waveform and electrocardiographic waveform obtained at the time of radiation treatment. Note that the user may input the irradiation conditions via the input interface 57.

By the implementation of the gantry control function 543, the processing circuitry 54 controls the gantry driving device 515 to emit radiation from an irradiation angle included in the irradiation conditions. The user may input the irradiation angle via the input interface 57.

By the implementation of the couch control function 544, the processing circuitry 54 controls the couch driving device 525 to move the treatment top plate 521 to an arbitrary position. The user may input the position of the treatment top plate 521 via the input interface 57. The processing circuitry 54 controls the couch driving device 525 so that the position of the treatment region of the patient coincides with an isocenter.

By the implementation of the display control function 545, the processing circuitry 54 displays various kinds of information via the display device 58. For example, the processing circuitry 54 displays treatment day images, a treatment plan screen, a treatment plan, a respiration guide, and the like.

The storage device 55 is a storage device such as a ROM, RAM, HDD, SSD, or integrated circuitry storage device that stores various kinds of information. The storage device 55 stores, for example, treatment day images, an electrocardiographic waveform, and a respiratory waveform that are obtained by the obtaining function 541. The storage device 55 may be a portable storage medium such as a CD, DVD, or flash memory, or a driver that reads and writes various kinds of information from and in a semiconductor memory element or the like, other than the above-mentioned storage device. The storage device 55 may be installed in another computer connected to the radiation treatment apparatus 5 via a network.

The communication interface 56 is an interface for performing information communication with the radiation treatment planning apparatus 4, the treatment day image acquiring apparatus 6, the respiratory waveform measuring device 7, and the electrocardiographic waveform measuring device 8.

The input interface 57 accepts various input operations from the user, converts the accepted input operations into electrical signals, and outputs them to the processing circuitry 54. More specifically, the input interface 57 is connected to an input device such as a mouse, keyboard, trackball, switches, buttons, joystick, touch pad, or touch panel display. The input interface 57 may be a voice input device using a voice signal from an input device such as a microphone that collects a voice. The input interface 57 may be a contactless input circuitry using an optical sensor. The input interface 57 outputs, to the processing circuitry 54, an electrical signal corresponding to an input operation to the input device. An input device connected to the input interface 57 may be an input device provided in another computer connected via a network or the like.

The display device 58 displays various kinds of information according to the display control function 545 of the processing circuitry 54. The display device 58 can be, for example, a LCD (Liquid Crystal Display), CRT display, OELD (Organic EL Display), plasma display, or another arbitrary display. The display device 58 may be a projector.

Next, an example of an operation of radiation treatment by the processing circuitry 54 of the radiation treatment apparatus 5 will be explained.

FIG. 12 is a flowchart showing a sequence of radiation treatment by the processing circuitry 54. At the start in FIG. 12, the treatment day image acquiring apparatus 6 has already performed medical photographing of a treatment target patient and generated treatment day images. A treatment plan has already been received from the radiation treatment planning apparatus 4. At the time of medical photographing, the respiratory waveform measuring device 7 has generated the respiratory waveform of the treatment target patient, and the electrocardiographic waveform measuring device 8 has generated the electrocardiographic waveform of the treatment target patient. At the start of step SB1 in FIG. 12, the patient is laid on the treatment top plate 521. In a series of processes of radiation treatment shown in FIG. 12, the respiratory waveform measuring device 7 has generated the respiratory waveform of the treatment target patient, and the electrocardiographic waveform measuring device 8 has generated the electrocardiographic waveform of the treatment target patient. In the radiation treatment shown in FIG. 12, deep inspiration breath hold irradiation is performed.

As shown in FIG. 12, the processing circuitry 54 first aligns the patient based on the treatment day images and treatment plan images by the implementation of the couch control function 544 (step SB1). For example, the processing circuitry 54 calculates a position error vector between a treatment day image and a treatment plan image about the same region, and controls the couch driving device 525 in accordance with the calculated position error vector to move the treatment top plate 521. In step SB1, the processing circuitry 54 may control the couch driving device 525 in accordance with an instruction by the user via the input interface 57 to move the treatment top plate 521. Only the patient laid on the treatment top plate 521 may be moved.

After step SB1, the processing circuitry 54 obtains a respiratory waveform and an electrocardiographic waveform by the implementation of the obtaining function 541 (step SB2). In step SB2, the processing circuitry 54 obtains in real time the respiratory waveform of the treatment target patient from the respiratory waveform measuring device 7 and the electrocardiographic waveform of the patient from the electrocardiographic waveform measuring device 8.

After step SB2, the processing circuitry 54 displays a respiration guide by the implementation of the display control function 545 (step SB3). In step SB3, the processing circuitry 54 displays a display screen representing the respiration guide on the display device 58. The display screen representing the respiration guide is displayed on the display device 58 installed at a position where the patient can see it.

Figure 13:
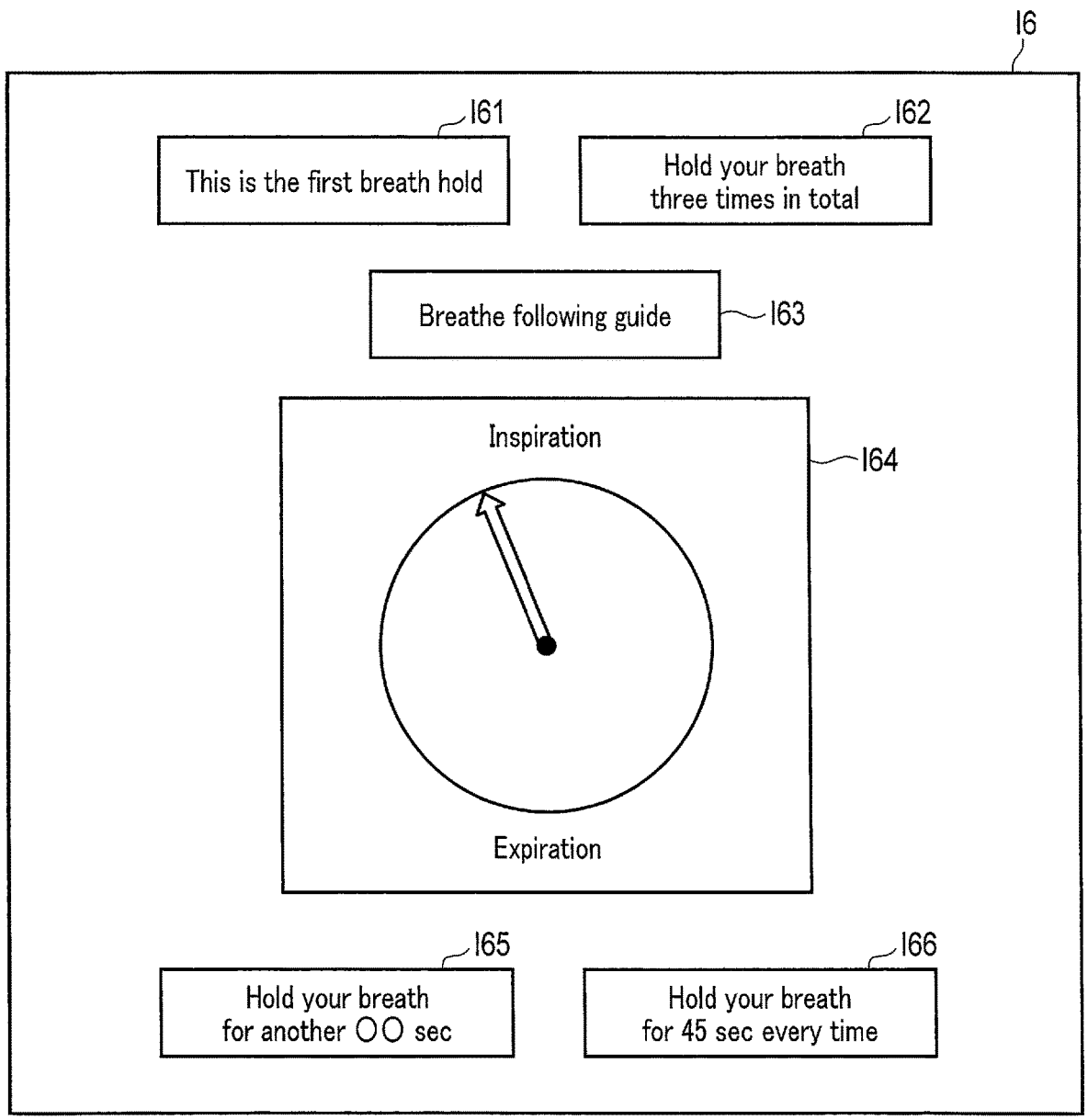
FIG. 13 is a view showing an example of a display screen representing a respiration guide.

FIG. 13 is a view showing an example of a display screen 16 representing a respiration guide. Note that the patient has breathed following the respiration guide at the start of step SB3. A current breath hold count such as "this is the first breath hold" is displayed in a display field I61. A total breath hold count such as "hold your breath three times in total" is displayed in a display field I62. A guide message such as "breathe following the guide" is displayed in a display field I63. A guide message corresponding the current respiration status of the patient is selected from a plurality of standard guide messages generated in advance, and displayed. The guide message may be selected by the user via the input interface 57, or the current respiration status of the patient may be automatically recognized to automatically select a guide message corresponding to the recognition result.

As shown in FIG. 13, a figure representing a breath timing is displayed in a display field I64. For example, a circle representing an inspiratory phase at the top and an expiratory phase at the bottom, and an arrow that rotates about the center of the circle serving as a pivot in the standard respiratory cycle of the patient are displayed. The patient breathes while watching the motion of the arrow. A remaining breath hold time such as "hold your breath for another ○○ sec" is displayed in a display field I65. Since the patient holds his/her breath at the start of step SB3, no remaining breath hold time is displayed in the display field I65. A breath hold time such as "hold your breath for 45 sec every time" is displayed in a display field I66. The total breath hold time and the breath hold time are decided in the treatment plan, read out from it, and displayed.

After step SB3, the processing circuitry 54 monitors the respiratory waveform and the electrocardiographic waveform by the implementation of the irradiation control function 542 (step SB4), and determines whether the current patient time phase is in the irradiation period (step SB5). In steps SB4 and SB5, the processing circuitry 54 specifies in real time the current respiratory time phase based on the peak value of the respiratory waveform obtained in real time, and specifies in real time the current cardiac phase based on the peak value of the electrocardiographic waveform. Then, the processing circuitry 54 decides a combination of the current respiratory time phase and the current cardiac phase as the current patient time phase.

After the preparation for deep inspiration breath hold irradiation, the user inputs a determination processing start instruction via the input interface 57. For example, when the breath hold of the patient starts, a determination processing start instruction is input. In response to the input of the determination processing start instruction, the processing circuitry 54 determines whether the current respiratory time phase is in the irradiation period decided in step SA5. For example, the irradiation period in deep inspiration breath hold irradiation is set in the respiratory time phase "inspiratory phase" and the cardiac phase "contraction phase". The processing circuitry 54 determines whether the current respiratory time phase is included in the respiratory time phase "inspiratory phase" and the cardiac phase "contraction phase" in the irradiation period.

If the processing circuitry 54 determines in step SB5 that the current patient time phase is not in the irradiation period (NO in step SB5), it repeats steps SB4 and SB5.

If the processing circuitry 54 determines that the current patient time phase is in the irradiation period (for example, the respiratory time phase "inspiratory phase" and the cardiac phase "contraction phase" in deep inspiration breath hold irradiation) (YES in step SB5), it emits radiation only in the irradiation period by the implementation of the irradiation control function 542 (step SB6). If no radiation can be emitted immediately after determining that the current patient time phase is in the irradiation period, radiation may be emitted after one or a plurality of heart beats.

Figure 14:
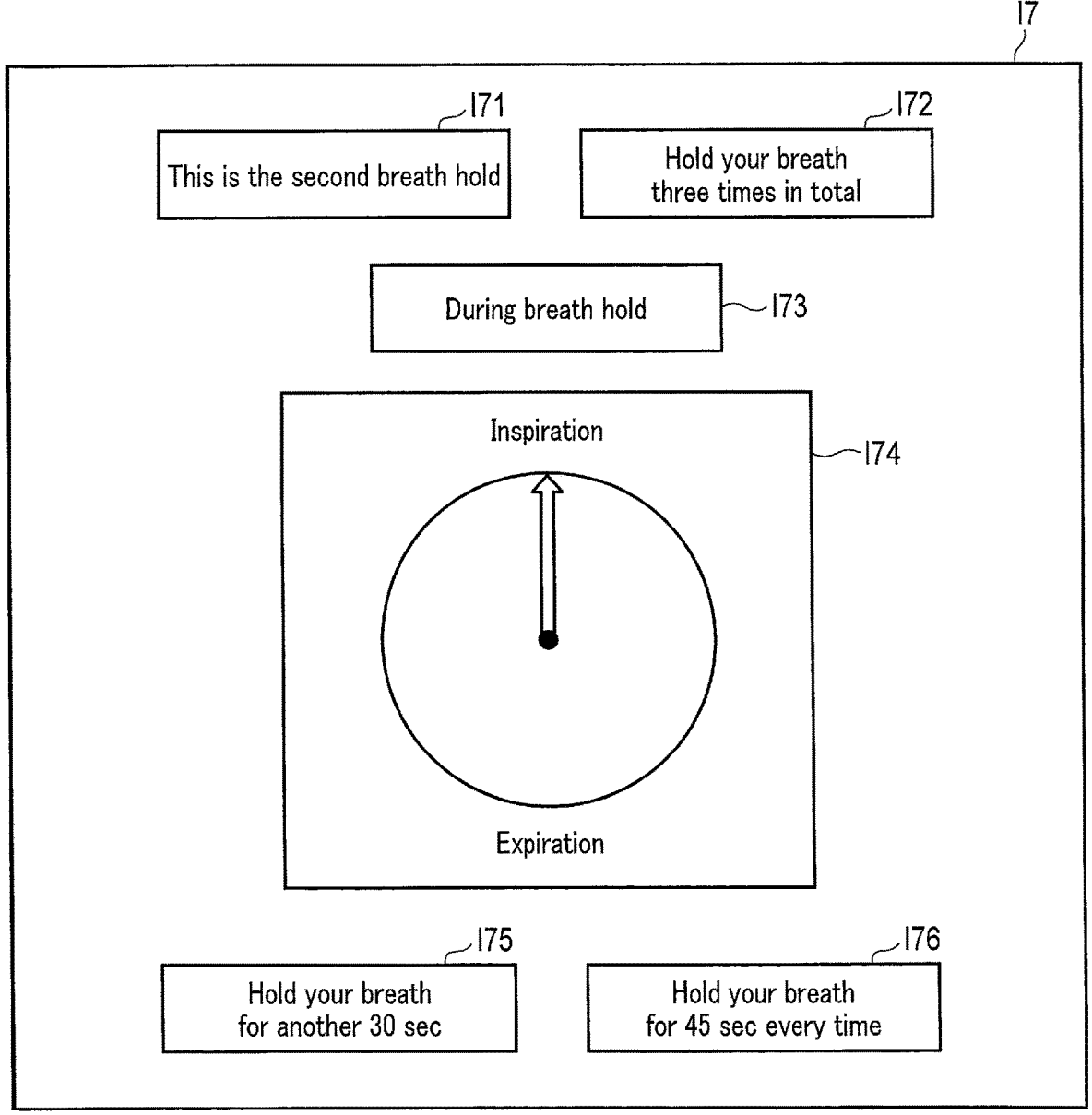
FIG. 14 is a view showing another example of a display screen representing a respiration guide.

FIG. 14 is a view showing an example of a display screen I7 representing a respiration guide. Note that the patient has held the breath at the time of displaying the display screen I7. A current breath hold count such as "this is the second breath hold" is displayed in a display field I71. A total breath hold count such as "hold your breath three times in total" is displayed in a display field I72. A guide message such as "during breath hold" is displayed in a display field I73. A figure representing a breath timing is displayed in a display field I74. A remaining breath hold time such as "hold your breath for another 30 sec" is displayed in a display field I75. A breath hold time such as "hold your breath for 45 sec every time" is displayed in a display field I76. By displaying the current breath hold count and the total breath hold count, the patient can grasp how many times he/she has to hold his/her breath, and get the peace of mind and the like. By displaying the remaining breath hold time and the breath hold time, the patient can grasp how long he/she has to hold his/her breath, and get the peace of mind and the like.

After step SB6, the processing circuitry 54 determines whether to end the irradiation by the implementation of the irradiation control function 542 (step SB7). If the irradiation dose has not reached a predetermined irradiation dose set in the treatment plan, the processing circuitry 54 determines in step SB7 not to end the irradiation (NO in step SB7). In this case, the processing circuitry 54 repeats steps SB4 to SB7 until the irradiation dose reaches the predetermined irradiation dose. If the irradiation dose reaches the predetermined irradiation dose, the processing circuitry 54 determines in step SB7 to end the irradiation (YES in step SB7). In this case, the processing circuitry 54 controls the irradiator 514 to stop the irradiation with the radiation. In deep inspiration breath hold irradiation, radiation irradiation at the predetermined irradiation dose cannot be completed by one breath hold and is completed by a plurality of breath holds.

After the stop of the irradiation with the radiation, the radiation treatment by the processing circuitry 54 ends.

Note that the sequence of processing regarding the radiation treatment shown in FIG. 12 can be changed variously. For example, the alignment in step SB1 may not be performed. In radiation treatment, the processing circuitry 54 may display on the same time axis a respiratory waveform measured by the respiratory waveform measuring device 7 and an electrocardiographic waveform measured by the electrocardiographic waveform measuring device 8, as shown in FIGS. 7 and 10 and the like. Further, the processing circuitry 54 may display the mark 25 indicating the breath hold release timing, the mark 27 indicating the breath hold start timing, and the like on the respiratory waveform and electrocardiographic waveform measured at the time of radiation treatment, as shown in FIGS. 7 and 10 and the like. From the display, the patient can clearly grasp the breath hold release timing and the breath hold start timing.

In step SB5, it is determined whether the current patient time phase is included in the irradiation period. Alternatively, it may be determined whether the current patient time phase is a patient time phase appearing a predetermined time before the irradiation period. The patient time phase appearing before the predetermined time is arbitrary, but may be set in, for example, the respiratory time phase "expiratory phase" and the cardiac phase "contraction phase" in deep inspiration breath hold irradiation.

In the above embodiment, no radiation is emitted in a period except the radiation irradiation period. However, in the period except the irradiation period, the processing circuitry 54 may control the leafs of the collimator of the irradiator 514, control the irradiation range not to irradiate an at-risk region with radiation, and emit radiation by the implementation of the irradiation control function 542. A treatment target region can be irradiated with radiation without increasing a dose applied to the at-risk region. Since the radiation non-irradiation period is shortened, the radiation irradiation time can be shortened.

The positions of the leafs are decided by the treatment plan generation function 413 of the processing circuitry 41 of the radiation treatment planning apparatus 4. With the treatment plan generation function 413, the processing circuitry 41 calculates such positions of the leafs as to satisfy the distance standard and/or the dose standard as for a time phase that does not satisfy the distance standard and/or the dose standard, out of a plurality of time phases. More specifically, as for the first distance standard, the processing circuitry 41 calculates the positions of the leafs at which the distance between the irradiation path and the at-risk region becomes equal to or larger than a predetermined value while ensuring a dose applied to the treatment target region. As for the dose standard, the processing circuitry 41 calculates the positions of the leafs at which the irradiation dose applied to the at-risk region becomes equal to or smaller than a predetermined value while ensuring a dose applied to the treatment target region.

As described above, the radiation treatment apparatus 5 includes the irradiator 514 and the processing circuitry 54. The irradiator 514 emits radiation. By the implementation of the obtaining function 541, the processing circuitry 54 obtains a treatment plan that is generated by the radiation treatment planning apparatus 4 and includes an irradiation period defined by a combination of a cardiac phase and a respiratory time phase. By the implementation of the irradiation control function 542, the processing circuitry 54 controls the irradiator 514 to emit radiation when the irradiation period includes a patient time phase defined by a combination of an electrocardiographic waveform changing with the pulsation of the heart of the patient and a respiratory waveform changing with the respiration that are obtained at the time of radiation treatment.

By the above-described arrangement, even when the positional relationship between a treatment target region and an at-risk region changes greatly along the pulsation of the heart and the respiratory motion, radiation can be emitted in an optimum cardiac phase and respiratory time phase. This can reduce a dose applied to the at-risk region.

According to at least one embodiment described above, a dose applied to an at-risk region such as the heart can be reduced.

The term "processor" used in the above description means, for example, a CPU, a GPU, or a circuitry such as an ASIC (Application Specific Integrated Circuitry), or a programmable logic device (for example, SPLD (Simple Programmable Logic Device), CPLD (Complex Programmable Logic Device), or FPGA (Field Programmable Logic Device)). The processor implements a function by reading out and executing a program saved in a storage circuitry. Note that a program may be directly incorporated in the circuitry of a processor instead of being stored in the storage circuitry. In this case, the processor implements a function by reading out and executing a program incorporated in the circuitry of the processor. In addition, the function corresponding to the program may be implemented by a combination of logic circuitry instead of executing the program. Note that each processor according to the embodiment may be formed as a single processor to implement its function by combining a plurality of independent circuitry in addition of being formed as single circuitry for each processor. Furthermore, a plurality of constituent elements in FIGS. 1, 2, and 11 may be integrated into one processor to implement the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiation treatment planning apparatus, comprising: processing circuitry configured to
    obtain time-series medical images;
    specify a first time phase in which radiation irradiation is performed and a second time phase in which no radiation irradiation is performed, in a period corresponding to the time-series medical images based on a positional relationship between a treatment target region and an at-risk region of a patient included in the time-series medical images, wherein the first time phase and the second time phase are defined by a combination of a cardiac phase associated with pulsation of a heart of the patient and a respiratory time phase associated with respiration of the patient; and
    generate a treatment plan based on at least one medical image of the specified first time phase, from among the time-series medical images,
    wherein the processing circuitry is further configured to cause a display to display a graph in which a first waveform changing with the pulsation of the heart of the patient obtained in imaging of the time-series medical images, and a second waveform changing with the respiration are represented on a same time axis, and display, in the graph, a mark indicating a cardiac phase and respiratory time phase corresponding to the first time phase.

2. The apparatus according to claim 1, wherein the processing circuitry is further configured to specify the first time phase and the second time phase based on a distance between the treatment target region and the at-risk region.

3. The apparatus according to claim 1, wherein the processing circuitry is further configured to specify the first time phase and the second time phase based on a distance between the at-risk region and an irradiation path of radiation passing through the treatment target region.

4. The apparatus according to claim 1, wherein the processing circuitry is further configured to specify the first time phase and the second time phase based on an amount of overlap between the at-risk region and an irradiation path of radiation passing through the treatment target region.

5. The apparatus according to claim 1, wherein the processing circuitry is further configured to specify the first time phase and the second time phase based on an irradiation dose to the at-risk region that is obtained from radiation passing through the treatment target region.

6. The apparatus according to claim 1, wherein the processing circuitry is further configured to specify a specific time phase that satisfies a distance standard and/or a dose standard, specify the first time phase based on the specified time phase, and specify as the second time phase a time phase excluding the first time phase in the period, the distance standard is a standard about a distance between the at-risk region and one of the treatment target region and an irradiation path of radiation passing through the treatment target region, and the dose standard is a standard about an irradiation dose to the at-risk region.

7. The apparatus according to claim 6, wherein the distance standard is defined by a standard in which the distance between the at-risk region and the irradiation path is not smaller than a first predetermined value, a standard in which the distance between the treatment target region and the at-risk region is not smaller than a second predetermined value, and/or a standard in which a volume or area of overlap between the irradiation path and the at-risk region is not larger than a third predetermined value.

8. The apparatus according to claim 1, wherein the processing circuitry is further configured to cause a display to distinctly display the first time phase and the second time phase.

9. The apparatus according to claim 1, wherein the processing circuitry is further configured to cause the display the graph so as to emphasize, in the graph, an irradiation period and/or stop period of radiation by a radiation treatment apparatus.

10. The apparatus according to claim 1, wherein the processing circuitry is further configured to display, in the graph, a mark indicating a time point at which breath hold is released and/or a time point at which breath hold starts.

11. The apparatus according to claim 1, wherein the processing circuitry is further configured to calculate a position of a leaf of a collimator mounted in a radiation treatment apparatus to satisfy a distance standard and/or a dose standard for a time phase that does not satisfy the distance standard and/or the dose standard in the period.

12. A radiation treatment planning apparatus, comprising: processing circuitry configured to
    obtain time-series medical images;
    specify a first time phase in which radiation irradiation is performed and a second time phase in which no radiation irradiation is performed, in a period corresponding to the time-series medical images based on a positional relationship between a treatment target region and an at-risk region of a patient included in the time-series medical images; and
    generate a treatment plan based on at least one medical image of the specified first time phase, from among the time-series medical images,
    wherein the processing circuitry is further configured to specify the first time phase and the second time phase based on an amount of overlap between the at-risk region and an irradiation path of radiation passing through the treatment target region.

13. A radiation treatment planning apparatus, comprising: processing circuitry configured to
    obtain time-series medical images;
    specify a first time phase in which radiation irradiation is performed and a second time phase in which no radiation irradiation is performed, in a period corresponding to the time-series medical images based on a positional relationship between a treatment target region and an at-risk region of a patient included in the time-series medical images; and
    generate a treatment plan based on at least one medical image of the specified first time phase, from among the time-series medical images,
    wherein the processing circuitry is further configured to specify a specific time phase that satisfies a distance standard and/or a dose standard, specify the first time phase based on the specified time phase, and specify as the second time phase a time phase excluding the first time phase in the period, the distance standard is a standard about a distance between the at-risk region and one of the treatment target region and an irradiation path of radiation passing through the treatment target region, the dose standard is a standard about an irradiation dose to the at-risk region, and the distance standard is defined by a standard in which the distance between the at-risk region and the irradiation path is not smaller than a first predetermined value, a standard in which the distance between the treatment target region and the at-risk region is not smaller than a second predetermined value, and/or a standard in which a volume or area of overlap between the irradiation path and the at-risk region is not larger than a third predetermined value.

14. The apparatus according to claim 13, wherein the dose standard is defined by a standard in which the irradiation dose applied to the at-risk region is not larger than a predetermined value.

* * * * *